United States Patent [19]

Snoke et al.

[11] 4,062,731

[45] Dec. 13, 1977

[54] PRODUCTION OF URICASE FROM MICROCOCCUS LUTEUS

[75] Inventors: Roy Eugene Snoke, Rochester, N.Y.; Hugh Arthur Risley, Newport Richey, Fla.; Charles Thomas Goodhue, Rochester, N.Y.

[73] Assignee: Eastman Kodak Company, Rochester, N.Y.

[21] Appl. No.: 707,459

[22] Filed: July 21, 1976

[51] Int. Cl.² ............................................. C12D 13/10
[52] U.S. Cl. ................................. 195/62; 195/66 R; 195/103.5 R
[58] Field of Search ................................ 195/62, 66 R

[56] References Cited

U.S. PATENT DOCUMENTS

| 3,431,176 | 3/1969 | Fukumoto et al. | 195/66 R |
|---|---|---|---|
| 3,475,276 | 10/1969 | Kano | 195/66 R |
| 3,620,923 | 11/1971 | Laboureur et al. | 195/66 R |
| 3,669,843 | 6/1972 | Aunstrup et al. | 195/66 R |
| 3,767,533 | 10/1973 | Sugisaki et al. | 195/66 R |
| 3,810,820 | 5/1974 | Laboureur et al. | 195/62 |

*Primary Examiner*—Lionel M. Shapiro
*Attorney, Agent, or Firm*—Arthur L. Girard

[57] ABSTRACT

A stable uricase preparation of high activity is produced by growing *Micrococcus luteus* NRRL B-8166 in a nutrient medium. Uricase preparations having activities of up to about 1000 U/liter are produced.

8 Claims, No Drawings

PRODUCTION OF URICASE FROM MICROCOCCUS LUTEUS

FIELD OF THE INVENTION

This invention relates to the isolation and purification of uricase from the soil microorganism *Micrococcus luteus*.

BACKGROUND OF THE INVENTION

Uricase is an enzyme capable of decomposing uric acid by oxidation to allantoin and hydrogen peroxide. This enzyme plays an important role in the medical field, especially in biochemical diagnosis where it is used as a reagent for the detection of uric acid in serum or urine.

Uric acid is one of the principle products of the catabolism of purine bases and of the materials which they contain, such as nucleic acids. If such catabolism does not take place or if elimination of the uric acid thus produced does not occur, accumulations of these products in the blood or body tissue can be the cause of many disorders, especially gout, certain forms of rheumatism, certain calculi in the region of the urinary system and various tissue changes, especially in the cardiovascular system. These disorders occur frequently because elimination of uric acid is rendered difficult by the very low solubility of this compound and increased concentrations of this compound due to any cause can bring about the formation of insoluble deposits.

Animal organs have heretofore been the principal source of uricase. Difficulties in extraction and purification or uricase from such sources have encouraged the development of uricase production from microorganisms. The production of uricase from various microorganisms, including bacteria, fungi and yeasts, is described in U.S. Pat. Nos. 3,431,176; 3,475,276; 3,620,923; 3,669,843; 3,767,533 and 3,810,820. It is likely that some trace of uricase might be found in any living organism but it cannot be predicted which organisms will yield uricase in sufficient quantities for any practical use.

U.S. Pat. Nos. 3,810,820 and 3,620,923 suggest that uricase may be obtained using bacteria of genus Micrococcus. However, no strains of bacteria of such genus have heretofore been identified as capable of providing useful levels of uricase in sufficient quantities to provide a commercially feasible source of uricase.

In the production of an enzyme such as uricase, whether by extraction from animal tissue or by fermentation of a microorganism, the desired enzyme is generally found in a liquid medium along with various other macromolecules such as proteins, including other enzymes, and/or other undesirable materials. Various methods have been used to purify the desired enzyme or separate it from at least some of the undesirable materials.

In purifying uricase, the enzyme, which is soluble in water but insoluble in organic solvents and insoluble in concentrated aqueous solutions of inorganic salts such as ammonium sulfate, can be recovered by precipitation either with an organic solvent which is miscible with water such as ethanol, methanol, isopropanol or acetone, or with a water soluble inorganic salt such as ammonium sulfate, mentioned previously. Salts or solvents can be removed by dialysis of a solution containing the redissolved precipitate.

Further purification can be accomplished, when necessary or desirable, by means of a series of precipitations from aqueous media, generally fractional precipitations, using organic liquids miscible with water or aqueous solutions containing ammonium sulfate. It is also possible to make use of adsorption upon hydroxyapatite, bentonite and alumina, and subsequent extraction, followed by elution using saline solutions. The purification can be carried still further by subjecting the thus treated products to chromatography, which may be a cyclic or noncyclic process, by making use of columns of substances which make it possible to eliminate those impurities, in particular, proteins, which are still present in the extract. The substances that can be used for this purpose include columns of cellulose ion exchange materials, dextrans and polyacrylamides. Elution may be effected by means of liquids in which there is a continuous or discontinuous change in the pH or in the molarity thereof.

SUMMARY OF THE INVENTION

The present invention provides a process for producing a stable, highly active uricase preparation. The process comprises the steps of growing the soil microorganism, *Micrococcus luteus* NRRL B-8166, in a growth medium to produce uricase and extracting the uricase from the medium. If the uricase as extracted from the growth medium is not pure enough for a particular use, it can be purified by ammonium sulfate precipitation and column chromatography.

DETAILED DESCRIPTION OF THE INVENTION

According to the present invention, a stable, highly active uricase preparation is obtained by growing the soil microorganism *Micrococcus luteus*. The *Micrococcus luteus* culture yielding high levels of such uricase is called NRRL B-8166 based on its deposit with the Agricultural Collection Investigations Fermentation Laboratory, Peoria, Ill.

A taxonomic identification of the microorganism follows:

Description of *Micrococcus luteus* NRRL B-8166 Microscopy

Phase and light-field microscopy were performed with a LABOROLUX laboratory microscope (Leitz) using a magnification of 700 ×.

Biochemical Tests

The gram stain, starch hydrolysis, indole, methyl red, catalase, oxidase, and $NO_3$-reduction tests were performed according to procedures of Blair et al "Manual of Chemical Microbiology," Williams and Wilkins, Co., Baltimore, Md., 1970. Sugar utilization was determined in commercially prepared medium or by adding 0.5% of filter-sterilized sugar solution (10% w/v) to sterile Durham tubes containing Phenol Red Broth Base (BBL). All tests were observed at 3-, 5-, and 7- day intervals.

Results

I. Microscopy
  A. Gram reaction — Gram-positive with a few gram-negative cells in older cultures.
  B. Morphology — Coccus, occurring mostly as single cells ca. $1\mu$ in diameter with a few pairs and tetrads, non-motile.
II. Colony morphology
  A. Nutrient agar slant — yellow pigment, filiform, smooth, glistening.

B. Nutrient agar plate — yellow pigment, circular, entire to serate, smooth, glistening, convex, raised colony.
C. Gelatin agar — Light yellow, small, circular, wrinkled, granulated colony with slight liquification.
D. Starch agar — Light yellow, small, smooth, round colony.
E. Potato — Thin, glistening yellow growth.
III. Agar stab — yellow surface growth (strict aerobe).
IV. Nutrient broth — sediment, ropy, no pellicle.
V. Aerobic acid production in Phenol Red Broth
   A. Arabinose — negative
   B. Raffinose — negative
   C. Xylose — negative
   D. Lactose — slight acid, no gas after 7 days
   E. Fructose — negative
   F. Dulcitol — negative
   G. Glycerol — negative
   H. Maltose — negative
   I. Trehalose — negative
   J. Galactose — negative
   K. Mannitol — negative
   L. Sucrose — negative
   M. Adonitol — negative
   N. Glucose — slight to no acid, no gas after 5 days
VI. Hydrolysis of
   A. Gelatin — slow crateriform liquification
   B. Starch — negative (5 days)
   C. Casein — negative (5 days)
VII. Other biochemical tests
   A. Litmus milk — slightly acid, no coagulation (5 days)
   B. $H_2S$ formation — negative on SIM and TSI agar
   C. Phosphatase — positive
   D. Indole — negative (5 days)
   E. Methyl-red — negative (5 days)
   F. Catalase — positive
   G. Oxidase — negative
   H. Urea utilization — negative (5 days)
   I. $NO_3$ reduction — positive
   J. Growth on $NH_4H_2PO_4$ as a sole nitrogen source (4 days) — negative
   K. Growth in 5% NaCl — positive
   L. Growth in 15% NaCl — negative
   M. Growth at 45° C — negative
   N. Phenylalanine — negative Unexpectedly, this strain of *Micrococcus luteus* produced surprisingly high levels of uricase on the order of above 1000 U/liter. The uricase thus produced is characterized by the following properties. It is a protein having a molecular weight of about 97,000 daltons. The uricase has maximum enzyme activity at pH 8.6 when using KPi buffer (potassium phosphate), and has a Michaelis constant of $3.7 \times 10^{-5}$ and an inhibition constant of $4.5 \times 10^{-6}$ M for oxonate. Cations inhibit the activity of the uricase of the present invention. Surprisingly $Co^{+2}$ and $Mn^{+2}$ have a greater inhibitory effect than $Cu^{+2}$. Unexpectedly, a biphasic inhibitory response rate curve for the cations $Co^{+2}$ and $Mn^{+2}$ was also found. The uricase showed some activation in the presence of phosphate or sulfate anions. After purification the uricase exhibited a specific activity of at least about 10.6 U. per mg. of protein.

A growth medium for cultivating the microorganism consists of the following nutrients; the concentration given based on 1 liter of medium is:

dibasic potassium phosphate: 2.0 g/l
uric acid: 5.0 g/l
yeast extract: 5.0 g/l
acetic acid: 5.0 g/l
salt solution: 10.0 ml/l.

where the salt solution consists of the following salts dissolved in water; the concentration in grams per liter of water is:

$MgSO_4 . 7H_2O$: 0.25
$MnSO_4 . H_2O$: 0.17
$FeSO_4 . 7H_2O$: 0.028
NaCl: 0.0006
$CaCl_2 . 2H_2O$: 0.001
$ZnSO_4 . 7H_2O$: 0.0006.

Of course the growth medium may be adjusted and modified by those skilled in the art in order to optimize the production of uricase. A temperature of about 30° C is useful for growing the bacteria cells.

After the cells are grown, they are separated from the fermentation broth by centrifugation or other suitable means. Yields of 0.014 to 0.016 g of cells (wet weight) per ml. growth medium have been obtained.

Uricase is extracted from the cells by suspending the cells in potassium phosphate (KPi) buffer containing ethylenediamine tetraacetic acid (EDTA). Generally, an extraction pH of about 8.6 has been found satisfactory, although the extraction may be successfully performed at higher or lower pH levels. To lyse the cells, aliquots of the suspension, cooled in a brine-ice bath, were sonicated using an ultrasonic probe. The disrupted cells were centrifuged to separate cell debris. The average yield of uricase, located in the supernatant fraction, was about 22 units per gram of cells (wet weight). The uricase extracted from the cells can be purified by conventional techniques such as ammonium sulfate fractionation, TEAE-cellulose chromatography and diafiltration.

The uricase solution obtained after purification can be freeze-dried or lyophilized for long term storage. A stable powdered uricase preparation is thus obtained, even without the use of added stabilizers.

The uricase preparation of this invention is useful for assaying for uric acid, particularly when using assay methods which use a hydrogen peroxide detection system. This uricase preparation is suitable for use in uric acid assays using both liquid analytical techniques and using dry test strip analytical techniques such as for example that described in Belgian Pat. No. 801,742 granted on Jan. 2, 1974 to Przybylowicz et al. Additional advantages will be appreciated by those skilled in the art upon consideration of the following examples which further illustrate the invention.

MAINTENANCE OF THE CULTURE

Isolated colonies of *Micrococcus luteus* NRRL B-8166 were transferred to agar slants containing nutrient medium comprising glucose, 1% yeast extract and 10 ml basal salt solution. The basal salt solution contained

|  | Grams/liter |
| --- | --- |
| $MgSO_4 . 7H_2O$ | 25.0 |
| $MnSO_4 . H_2O$ | 17.0 |
| $FeSO_4 . 7H_2O$ | 2.8 |
| NaCl | 0.06 |
| $CaCl_2 . 2H_2O$ | 0.10 |

-continued

| | Grams/liter |
|---|---|
| $ZnSO_4 \cdot 7H_2O$ | 0.06 |

The slants were incubated for 2 days at 30° C and then stored at 4° C until used.

EXAMPLE 1

Growing Microorganism to Produce Uricase

A slant of *Micrococcus luteus* NRRL B-8166 was transferred to a 125 ml. flask containing 25 ml. of growth medium. The growth medium contained, per liter of medium, Dibasic potassium phosphate: 2 g
Uric acid: 5 g
Yeast extract: 5 g
Acetic acid: 5 g
Basal salt solution: 10 ml.

The pH value was adjusted to 7.0 with KOH. The cells were grown for 24 hours at 30° C with shaking at 200 rpm (2 inch throw) and then transferred to 1 liter flasks containing 500 ml medium. The cells were grown for 22 hours at 30° C with shaking at 100 rpm and then collected by centrifugation at 13,700 $\times$ g for 15 minutes. The yield was 0.014 – 0.016 g cells (wet weight) per ml. growth medium.

A 10% (w/v) suspension of cells in 50 mM potassium phosphate (KPi) buffer, pH 8.6, containing $10^{-4}$M ethylenediamine tetraacetic acid (EDTA) was prepared. To lyse the cells, 50 ml aliquots of the suspension, cooled in a brine-ice bath, were sonicated for 10 minutes using a probe with standard tip (Ultrasonics, Inc., Plainview, N.J.) powered by a J-17A power supply operating at setting 5 (Branson Sonic Power Co., Danville, Conn.). The disrupted cells were centrifuged at 27,000 $\times$ g to precipitate cell debris. The average yield of uricase, located in the supernatant fraction, was 22 units per g cells (wet weight).

MAKING CHROMATOGRAPHIC COLUMN MATERIAL BY IMMOBILIZATION OF 1,6-DIAMINOHEXANE ON AGAROSE

A stirred slurry of 100 ml agarose (available commercially as Sepharose 4B from Pharmacia Fine Chemicals) and 100 ml of distilled water was cooled in an ice bath to 20° C and the pH was adjusted to 11 with 6 M sodium hydroxide, 24 g of cyanogen bromide (~250 mg/ml) was added to the slurry and the pH was maintained at 11±0.2 by dropwise addition of 6 M sodium hydroxide. Ice was added directly to the reaction mixture as needed to maintain the temperature at 20±4° C. The reaction mixture was stirred for 30 minutes (addition and reaction time) and the solid product was recovered by vacuum filtration on a sintered glass funnel. The product was washed with cold 0.1 M potassium phosphate buffer adjusted to pH 10. The cyanogen bromide-activated agarose was added to 300 ml of 0.1 M phosphate buffer (pH 10) containing (0.05 mole) 1,6-diaminohexane. The reaction mixture was stirred for 24 hours at 4° C. The solid product was collected by vacuum filtration, washed with a liter of distilled water, and added to 100 ml of the potassium phosphate buffer containing 20 ml of ethanolamine. The slurry was stirred for 24 hours at 4° C. The product was collected, washed with distilled water until the wash was free of amine (using the 2,4,6-trinitrobenzene sulfonate test) and stored in the refrigerator in 100 ml of the potassium phosphate buffer.

EXAMPLE 2

Purification of Enzyme Solution

A. Ammonium Sulfate Fractionation — All subsequent steps were performed at 4° C. Solid ammonium sulfate (0.351 g/ml) was added slowly with stirring to the enzyme solution prepared in Example 1. After 1 hour, the material was centrifuged at 27,000 $\times$ g for 20 minutes. Enzyme was in the supernatant fraction (I). Ammonium sulfate (0.141 g/ml) was added to this fraction, and after 1 hour, the sample was centrifuged as before. Both uricase and catalase activities were contained in the pellet fraction (II); this material was then dissolved in 0.22 ml KPi buffer, pH 8.6, per ml of original volume of fraction I.

B. Amphiphilic Column Chromatography — In order to remove the unwanted catalase activity, the solution containing the redissolved ammonium sulfate pellet was chromatographed by amphiphilic chromatography using the 1,6-diaminohexane-agarose material as prepared above.

The dissolved ammonium sulfate pellet was diluted with four volumes of 50 mM KPi at a pH of 8.6 containing $10^{-4}$M EDTA. The dilute solution was applied to a 2.8 cm $\times$ 9 cm column of the 1,6-diaminohexane- agarose equilibrated with KPi buffer. The column was washed with four column volumes of this buffer. Next the column was eluted twice, each time with two column volume aliquots of 0.5 M NaCl in KPi buffer containing $10^{-4}$ EDTA and 0.5% (v/v) Tergitol 15-S-7. Approximately 80% of the uricase activity was assayed in the combined fractions. Finally the column was eluted with four column volumes of 2.0 M NaCl in the KPi-EDTA-Tergitol buffer solution. The combined fractions for this elution contained no detectable uricase and substantially all the catalase activity of the crude enzyme solution.

C. TEAE-Cellulose Chromatography — The fractions containing uricase were diluted with KPi-EDTA buffer, pH 8.6, to a final salt concentration of 0.3 M NaCl and applied to a triethylaminoethyl-cellulose column (2.8 cm $\times$ 9 cm). Uricase was eluted from the column with two column volumes of KPi-EDTA buffer, pH 8.6, containing 0.5 M NaCl. This sample, free of surfactant, was concentrated in an Amicon diaflo cell fitted with a PM-10 membrane, and then dialyzed overnight against the KPi-EDTA buffer, pH 8.6. This enzyme preparation can be freeze-dried (lyophilized) and stored as a dry powder until ready for use.

A representative isolation of uricase purified according to the above procedure, but using two ammonium sulfate fractionation steps, is presented in Table I. The overall recovery of this purification process was 73 percent of the starting uricase activity.

Table I

Purification of Uricase From *Micrococcus Luteus*

| Sample | Total Units Uricase | Total Units Catalase | Uricase Recovery % | Uricase Specific Activity U per mg Protein | Protein mg/ml |
|---|---|---|---|---|---|
| Sonicated Supernatant | 663 | 1,125,517 | 100 | 1.20 | 1.62 |
| Ammonium Sulfate I | 542 | 251,438 | 82 | —[a] | —[a] |
| Ammonium Sulfate II | 490 | 288,000 | 74 | 2.87 | 1.96 |
| Diaminohexane-Agarose Column Eluate | 543 | 0 | 82 | —[a] | —[a] |
| TEAE-Cellulose Column Eluate | 484 | 0 | 73 | 10.6 | 0.122 |

[a]Samples not analyzed

ASSAY OF URICASE

Uricase was assayed spectrophotometrically by following the disappearance of uric acid at 290 nm using a modification of the procedure described by Mahler et. al, J. Biol. Chem., p. 625, 216 (1955). Assay tubes contained 2.7 ml 50 mM KPi buffer pH 8.6, 0.1 mM sodium EDTA, 0.05 ml 6 mM urate, plus enzyme and water to give a final volume of 3.0 ml. Changes or additions to the assay mixtures were made when necessary. Tubes were incubated for 5 minutes at 30° C; the reaction was started by adding enzyme. Molar extinction coefficient for uric acid at 290 nm is 12,300. Activity was expressed in units of uricase activity, where a unit is that amount of enzyme which catalyzes the oxidation of one $\mu$mole of uric acid per minute at 30° C and pH 8.6.

EFFECTS OF METAL IONS, SALTS AND SOME SURFACTANTS ON URICASE FROM MICROCOCCUS LUTEUS

A. Cations

Uricase was assayed as previously described except that 50 mM Tris-Cl, pH 8.6, was the assay buffer used. The cations, as indicated in Table II, were added to the reaction cuvettes as the chloride salt dissolved in water. Enzyme activity is expressed as percent of the activity assayed without added cations which is 0.52 $\mu$moles uric acid oxidized per minute per ml enzyme solution.

Table II

| Cation | mM | Activity |
|---|---|---|
| None | — | 100 |
| $Fe^{+3}$ | 0.1 | 72 |
| $Cu^{+2}$ | 0.1 | 62 |
| $Co^{+2}$ | 0.1 | 19* |
| $Mn^{+2}$ | 0.1 | 37* |
| $Mg^{+2}$ | 0.1 | 111 |

*biphasic response, slow initial catalytic rate rapidly followed by complete inhibition.

Unlike other known bacterial uricase activities, copper was not the most inhibitory cation. Instead, cobalt and manganese ions were the most effective, but their inhibition patterns were unusual in that both cations gave a biphasic rate curve with a slow initial rate followed by complete inhibition of catalysis at a concentration of $10^{-4}$ M. This pattern of response has not been reported before, and indicates that unique properties may exist for this enzyme protein.

B. Other Salts

Phosphate and sulfate substantially activated uricase while acetate and chloride had little effect. But, nitrate significantly lowered uricase activity when included in the reaction mixture. These activity modifications were rather complex and indicated more than just an ionic strength effect.

Although sodium chloride seemed to have minimal effects on the activity of uricase, the enzyme was influenced by the salt concentration, and again the extent of the effects was dependent upon the buffer used in the assay. Uricase assayed in Tris-buffered systems was the least sensitive to sodium chloride (the chloride content of buffer alone was negligible). However, uricase assayed in KPi-buffered systems was very sensitive to increased salt levels, with greater than 50 percent inhibition observed at 100 mM salt. This effect of phosphate differed from the enzyme stabilizing effect usually observed for KPi. Such sensitivity could be important when testing this uricase as an analytical reagent for serum urate since sodium chloride content of normal serum is 0.15 M.

EXAMPLE 3

Solution Assay of Serum Uric Acid

The uricase which we have isolated from *Micrococcus luteus* is shown to quantitatively assay the urate content of biological solutions, as uricase activities from other sources are known to do, by catalyzing the following reaction.

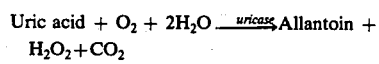

$$\text{Uric acid} + O_2 + 2H_2O \xrightarrow{uricase} \text{Allantoin} + H_2O_2 + CO_2$$

Materials

Validate (a serum standard) was purchased from General Diagnostics Division, Warner Lambert Co., Morris Plains, N.J. All other chemicals were of the best quality commercially available. All solutions were made with demineralized deionized water.

PROCEDURE

The assay mixture contained 50 mM KPi buffer, pH 8.6; 1 mM EDTA; and enough enzyme to oxidize 99% of the substrate in 5 minutes. The urate concentration used to calculate the required uricase level was 0.83 mg/dl (5 × $10^{-5}$ M).

Two solutions, one containing 5 $\mu$l and the other 25 $\mu$l of urate solution (40.5 mg/dl) were run at pH 8.6 and 30° C. The change in absorbance was followed at 290 nm. The oxidation of normal levels (3-7 mg/dl) and high levels (~15 mg/dl) of urate were completed within the desired time (5 min).

SERUM ANALYSIS

A solution of uric acid in 50 mM KPi buffer, pH 8.6 (40.5 mg/dl) and a sample of the commercially prepared serum standard, Validate, were prepared. Aliquots of these solutions were added to tubes containing 2.7 mg of 50 mM KPi, pH 8.6, $10^{-3}$ M EDTA and 0.14 units of uricase. The changes in optical density at 290 nm and 30° C were used to calculate the uric acid levels. Good assays were obtained.

The invention has been described in detail with particular reference to certain preferred embodiments thereof, but it will be understood that variations and modifications can be effected within the spirit and scope of the invention.

We claim:

1. A process for producing uricase which comprises growing *Micrococcus luteus* NRRL B-8166 in a medium to produce to uricase, and separating the uricase from the medium.

2. The process for producing uricase as defined in claim 1 wherein the separating step includes ammonium sulfate precipitation and chromatography.

3. A uricase preparation comprising an uricase having the following properties:
   a molecular weight of about 97,000 daltons;
   maximum activity at a pH of 8.6, in a potassium phosphate buffer;
   a Michaelis constant of $3.7 \times 10^{-5}$;
   an inhibition by $Fe^{+3}$, $Cn^{+2}$, $Co^{+2}$, or $Mn^{+2}$;
   a biphasic inhibitory response rate curve to $Co^{+2}$ or $Mn^{+2}$; and
   activation by $PO_4^{-3}$ or $SO_4^{-2}$.

4. The uricase preparation of claim 3 further having a specific activity of at least 10.6 U. per mg. of protein.

5. The uricase preparation of claim 3 which is lyophilized to form a dry powder.

6. An uricase preparation comprising a uricase
   a molecular weight of about 97,000 daltons;
   a maximum activity at a pH of 8.6, in a potassium phosphate buffer;
   a Michaelis constant of $3.7 \times 10^{-5}$;
   an inhibition by $Fe^{+3}$, $Cn^{+2}$, or $Mn^{+2}$;
   a biphasic inhibitory response rate curve to $Co^{+2}$ or $Mn^{+2}$; and
   activiation by $PO_4^{-3}$ or $SO_4^{+2}$ and obtained by growing *Micrococcus luteus* NRRL B-8166.

7. The uricase preparation of claim 6 further having a specific activity of at least 10.6 U. per mg. of protein.

8. The uricase preparation of claim 6 which is lyophilized to form a dry powder.

* * * * *